(12) United States Patent
Sogaro

(10) Patent No.: US 8,109,387 B2
(45) Date of Patent: Feb. 7, 2012

(54) DEVICE FOR APPLYING FLOWABLE SUBSTANCES

(75) Inventor: Alberto C. Sogaro, Kronberg (DE)

(73) Assignee: Sulzer Mixpac AG, Haag (CH)

( * ) Notice: Subject to any disclaimer, the term of this patent is extended or adjusted under 35 U.S.C. 154(b) by 533 days.

(21) Appl. No.: 12/038,489

(22) Filed: Feb. 27, 2008

(65) Prior Publication Data

US 2008/0230408 A1 Sep. 25, 2008

(30) Foreign Application Priority Data

Mar. 20, 2007 (EP) ..................... 07005695

(51) Int. Cl.
- *B65D 83/10* (2006.01)
- *A61M 35/00* (2006.01)
- *A46B 11/00* (2006.01)
- *B43K 5/14* (2006.01)

(52) U.S. Cl. ................... 206/361; 604/1; 604/2; 604/3; 401/118; 401/132

(58) Field of Classification Search ............... 604/1, 2, 604/3; 206/222, 229; 401/132

See application file for complete search history.

(56) References Cited

U.S. PATENT DOCUMENTS

| | | | |
|---|---|---|---|
| 3,690,448 A * | 9/1972 | Switzer | 206/361 |
| 4,747,719 A | 5/1988 | Parkin | |
| 5,112,152 A * | 5/1992 | McBride | 401/132 |
| 5,704,906 A | 1/1998 | Fox | |
| 6,036,005 A * | 3/2000 | Krause et al. | 206/221 |
| 6,516,947 B1 * | 2/2003 | Van Dyke et al. | 206/361 |
| 6,746,169 B2 * | 6/2004 | Muller | 401/134 |
| 2002/0197094 A1 * | 12/2002 | Gruenbacher et al. | 401/133 |
| 2003/0004089 A1 | 1/2003 | Huber et al. | |
| 2003/0233063 A1 * | 12/2003 | Nakatani | 604/2 |
| 2004/0134815 A1 | 7/2004 | Discko, Jr. | |
| 2009/0152267 A1 * | 6/2009 | May et al. | 220/23.83 |

FOREIGN PATENT DOCUMENTS

DE 20020049 U1 4/2001

* cited by examiner

*Primary Examiner* — Tatyana Zalukaeva
*Assistant Examiner* — Susan Su
(74) *Attorney, Agent, or Firm* — Quarles & Brady LLP

(57) ABSTRACT

A device for applying a liquid, pasty or other flowable substance includes a pack with a receiving section comprising a wet portion for receiving the substance and a closure section defining a dry portion. The closure section is separated from the receiving section by a tear line. The wet portion is separated from the dry portion by means of a separation element comprising an orifice closed off by a closure element which is releasable from the separation element after tearing open the pack along the tear line.

16 Claims, 5 Drawing Sheets

DEVICE FOR APPLYING FLOWABLE SUBSTANCES

CROSS REFERENCES TO RELATED APPLICATIONS

This application claims the priority benefit of European Patent Application No. 07 005 695.7, which was filed on Mar. 20, 2007, and is fully incorporated herein by reference.

STATEMENT REGARDING FEDERALLY SPONSORED RESEARCH

Not Applicable.

FIELD OF INVENTION

The invention relates to a device for applying liquid, pasty or other flowable substances.

BACKGROUND OF INVENTION

One such device is known in prior art, configured, for example, in the form of a brush, by means of which the flowable substance which, for instance, is a liquid such as acetone or some other substance as put to use in medical or dental applications, can be applied. The flowable substance or liquid is held as a rule in a receptacle into which the brush is dipped in application, so that the hair of the brush is wetted with the liquid. In this arrangement, brush and receptacle are held separately from a user.

SUMMARY OF THE INVENTION

The invention is based on the object of providing a device for applying liquid, pasty or other flowable substances which is characterized by its use now being particularly simple.

This object is achieved in accordance with the invention by a device having a pack with a receiving section comprising a wet portion for receiving the substance and a closure section defining a dry portion, the closure section being separated from the receiving section by a tear line, the wet portion being separated from the dry portion by a separation element, comprising an orifice closed off by a closure element which is releasable from the separation element after tearing open the pack along the tear line.

Thus, in accordance with the invention a device for applying a liquid, pasty or other flowable substance is proposed, including a pack with a receiving section comprising a wet portion for receiving the substance and a closure section defining a dry portion, the closure section being separated from the receiving section by a tear line, the wet portion being separated from the dry portion by means of a separation element, comprising an orifice closed off by a closure element which is releasable from the separation element after tearing open the pack along the tear line.

In accordance with a preferred embodiment a device for applying a liquid, pasty or other flowable substance is proposed, including a pack with a receiving section comprising a wet portion for receiving the substance and a closure section defining a dry portion, the closure section being separated from the receiving section by a tear line, an applicator fully incorporated in the pack and featuring an application section and a finger grip section located in the dry portion of the pack, the wet portion being separated from the dry portion by means of a separation element, comprising an orifice closed off by the applicator for engaging the application section of the applicator in the wet portion.

The device in accordance with the invention thus comprises in the form of the receiving section a wet portion and in the form of the closure section a dry portion in which the finger grip section of the applicator configured, for example, as a brush or the like is arranged.

In a special embodiment the application section which, among other things, may be a brush, a flock coating or a foam, and may be bonded or molded to the finger grip section, dips into the wet section in thus being wetted with the substance to be applied even before use of the device. In use, first the closure section is separated from the receiving section by tearing open the receptacle along the tear line. Then, all that needs to be done is to pull the applicator from the sealing means and the receiving space for the substance to be applied in enabling the substance to be applied directly to the site to be wetted thereby.

The substance to be applied is trapped within the device in the receiving space and is unable to spread in the pack as a whole, particularly not in the closure section or dry portion of the pack. Opening up the pack exposes the clean finger grip section of the applicator to the user.

In another preferred embodiment of the device in accordance with the invention to securely position the separation element within the pack, it is sealed to the pack. This is particularly possible when the separation element is made of plastics material and the pack is likewise made of a plasticized material.

In yet another preferred embodiment which is suitable, for example, to pack acetone or the like, the separation element is a receptacle defining a receiving space, forming a primary pack for the flowable substance and the pack forms a secondary pack for the flowable substance.

For example, the receptacle is a tubular part closed off at one end, defining the receiving space and which is connected to the pack in the region of its closed end. Particularly, the tubular part is welded to the pack in the region of its closed end, the tubular part then forming the primary pack for the flowable substance, the pack representing a secondary pack or repackage.

In another special embodiment the application section of the applicator dips into the wet portion, passing through the finger grip section of the applicator in sealing the orifice of the separation element.

As an alternative, the application section of the applicator may also be located in the dry portion, the finger grip section of the applicator closing off the orifice of the separation element by its end facing away from the application section. This embodiment is particularly useful when the flowable substance held by the device can attack the application section of the applicator to, for example, dissolve a bond between the application section and the finger grip section in extended contact.

The finger grip section may form a plug for the orifice of the separation element. As an alternative, the finger grip section can be produced in one piece with the separation element from which it is separated by a designed frangible location so that parting the applicator from the separation element releases its orifice.

The device in accordance with the invention is particularly simple to produce when the pack is formed by two foil blanks edge-sealed on all sides. The foil blanks may each be made of a foil laminate, for example an aluminum laminate. Making the pack of an aluminum laminate is also suitable for safely packaging acetone or other aggressive substances.

To safeguard the sealing means in the pack the foil blanks may comprise a sealing seam oriented crosswise to the centerline of the applicator, level with the sealing means.

In another example embodiment of the device in accordance with the invention the tear line which must not necessarily be an explicitly defined line, but may change depending on the force required to tear the pack open, is defined by at least one side tear nick in the foil blanks. The tear nick is expediently located in the region of the seam sealing the two foil blanks on all sides.

In still another special embodiment in which no primary pack and secondary pack is needed and the receiving space for the flowable substance is directly defined by the pack or the foil blanks thereof, the separation element may also be a disc-type plastics insert having a center hole or recess, the diameter of which corresponds to a shank of the applicator means. The plastics insert may be lenticular in shape. In one special embodiment of the device in accordance with the invention the sealing means is a tubular part through which the applicator means passes. This tubular part configured in the form of a sleeve is sealed to the material of the pack.

To hold the applicator secure in the sealing means, the applicator, may comprise an inner groove which is engaged by the sealing means. As an alternative it is, of course, just as possible that the applicator, comprises a ring bead which engages a ring groove in the sealing means.

Furthermore, the finger grip section of the applicator may be knurled to ensure secure location of the applicator in the separation element.

Further advantages and advantageous aspects of the device in accordance with the invention read from the description, the drawing and the claims.

BRIEF DESCRIPTION OF THE DRAWINGS

Referring now to the drawing there is illustrated diagrammatically simplified three example aspects of the device in accordance with the invention which will now be detailed with reference to the drawing in which.

DETAILED DESCRIPTION OF THE PREFERRED EMBODIMENT

Figure 1:
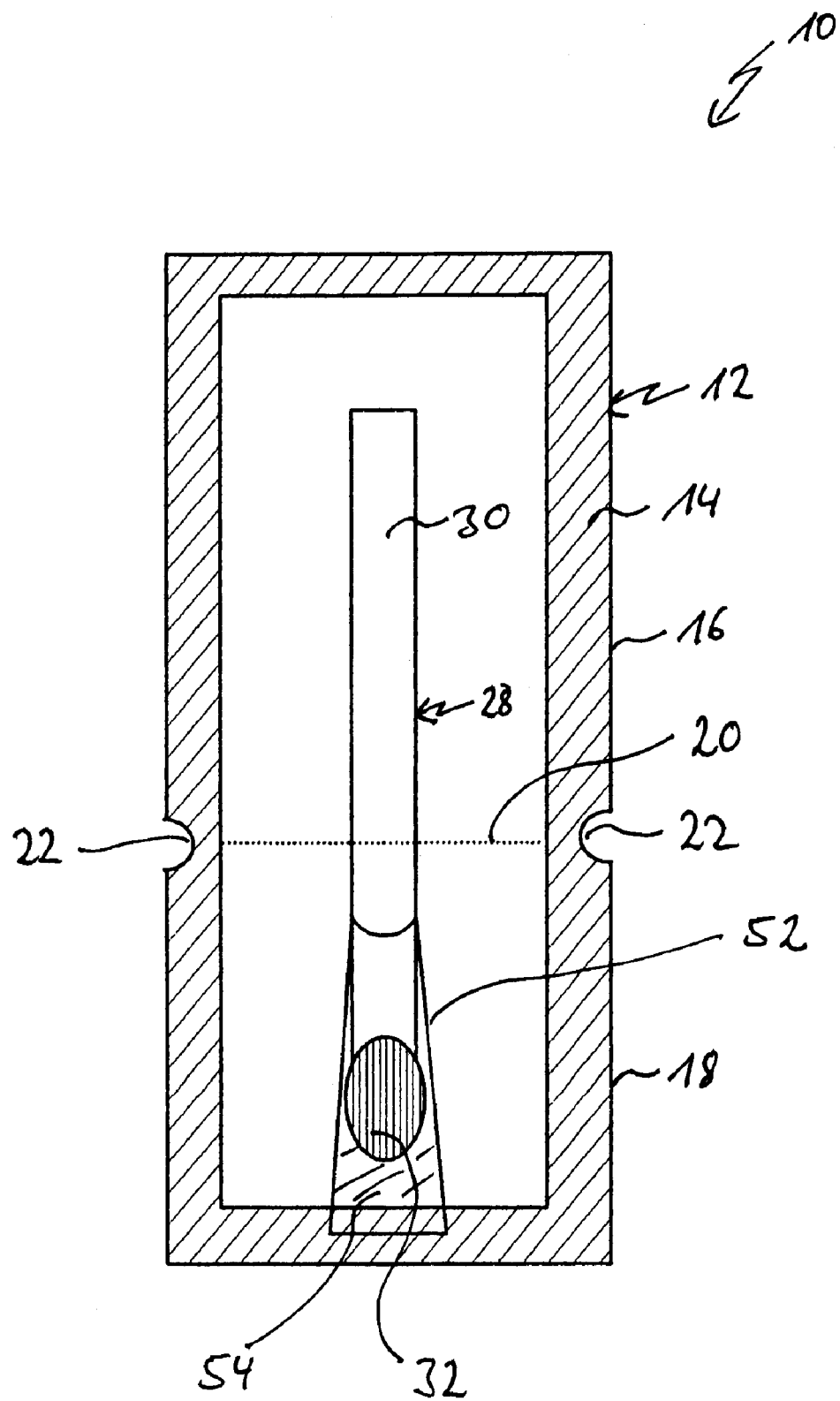
FIG. 1 is a diagrammatic illustration of a pack-type device in accordance with the invention including an applicator means.

Referring now to FIG. 1 there is illustrated a device 10 for receiving and applying a flowable substance such as acetone, as may find application, for example in dental treatment.

The device 10 comprises a substantially rectangular pack 12 made of two blanks of aluminum laminate foil, edge sealed on all sides at edge portion 14. The pack 12 comprises a closure section 16 defining a dry portion and a receiving section 18 comprising a wet portion, closure section 16 and receiving section 18 being separated from each other by a tear line 20 defined by nicks 22 disposed on both sides in the region of the edge portion 14 representing a edge sealing seam. The tear line 20 may be formed by a weakening of the material of the foil blanks or materialize when tearing open the pack at one of the nicks 22.

The device 10 comprises in addition a tube 52 representing a receptacle defining a receiving space 54 of the receiving section 18 of the pack 12 forming the wet portion and a separation element between the dry portion and wet portion.

The applicator 28 is inserted by an application section 32 into the tube 52 so that the application section 32 dips into the flowable substance held by the tube 52.

The tube 52 which thus defines the wet portion of the device 10 in forming a receptacle is welded by its end facing away from the finger grip section 30 of the applicator 28, i.e. by its bottom end, in the sealing seam on all sides of the pack 12. Since at least the end portion of the tube 52 facing the bottom end has an inner diameter corresponding to the diameter of the finger grip section 30 of the applicator 28, the tube 52 itself seals the receiving space 54 forming the wet portion from the dry portion located within the pack 12 and surrounding the finger grip section 30 of the brush-type applicator and the tube 52. Accordingly, no liquid can escape from the receiving space 54 and gain access to the dry portion and spread within the pack 12. After the pack 12 is torn open along the tear line 20 defined by the nicks 22 a clean finger grip section 30 of the applicator 28 is thus exposed.

When use is made of the device 10, the user tears the pack 12 open along the tear line 20 and removes the closure section defining the closure section 16 so that the clean finger grip section 30 of the applicator 28 is exposed. The user then draws the brush 28 from the tube 52 so that the application section 32 of the brush 28 wetted with the substance to be applied can be brought into contact with an application site.

Figure 2:
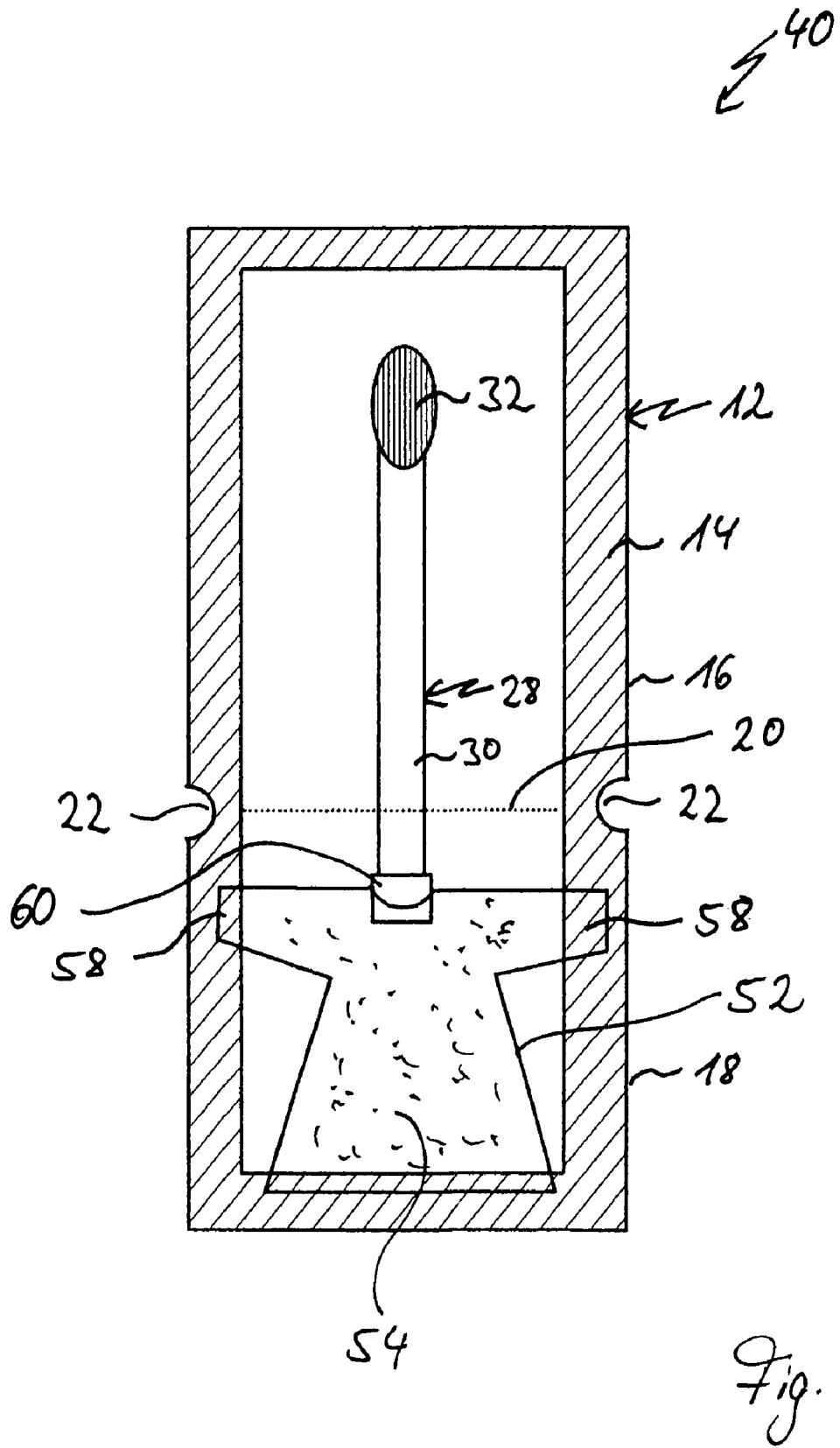
FIG. 2 is a diagrammatic illustration of a second embodiment of a pack-type device.

Referring now to FIG. 2 there is illustrated a further embodiment of a device 40 for applying a flowable substance to an application site. The device 40 is substantially the same as that as shown in FIG. 1, but differs therefrom in that the application section 32 of the applicator 28 is located in the dry portion of the pack 12, the finger grip section 30 plugging the orifice of the receptacle or tube 52 by its end section 60 facing away from the application section 32. The orifice may comprise (not shown) an insertion funnel for the brush hair of the applicator 28.

In addition, for secure seating in the pack 12 the tube 52 has protuberances 58 welded in the sealing seams of the pack 12, resulting in the receptacle being connected to the pack in three portions, namely in its bottom portion and in the portions of its protuberances 58 or webs. It will be appreciated that this is just as possible in the embodiment as shown in FIG. 1.

Figure 3:
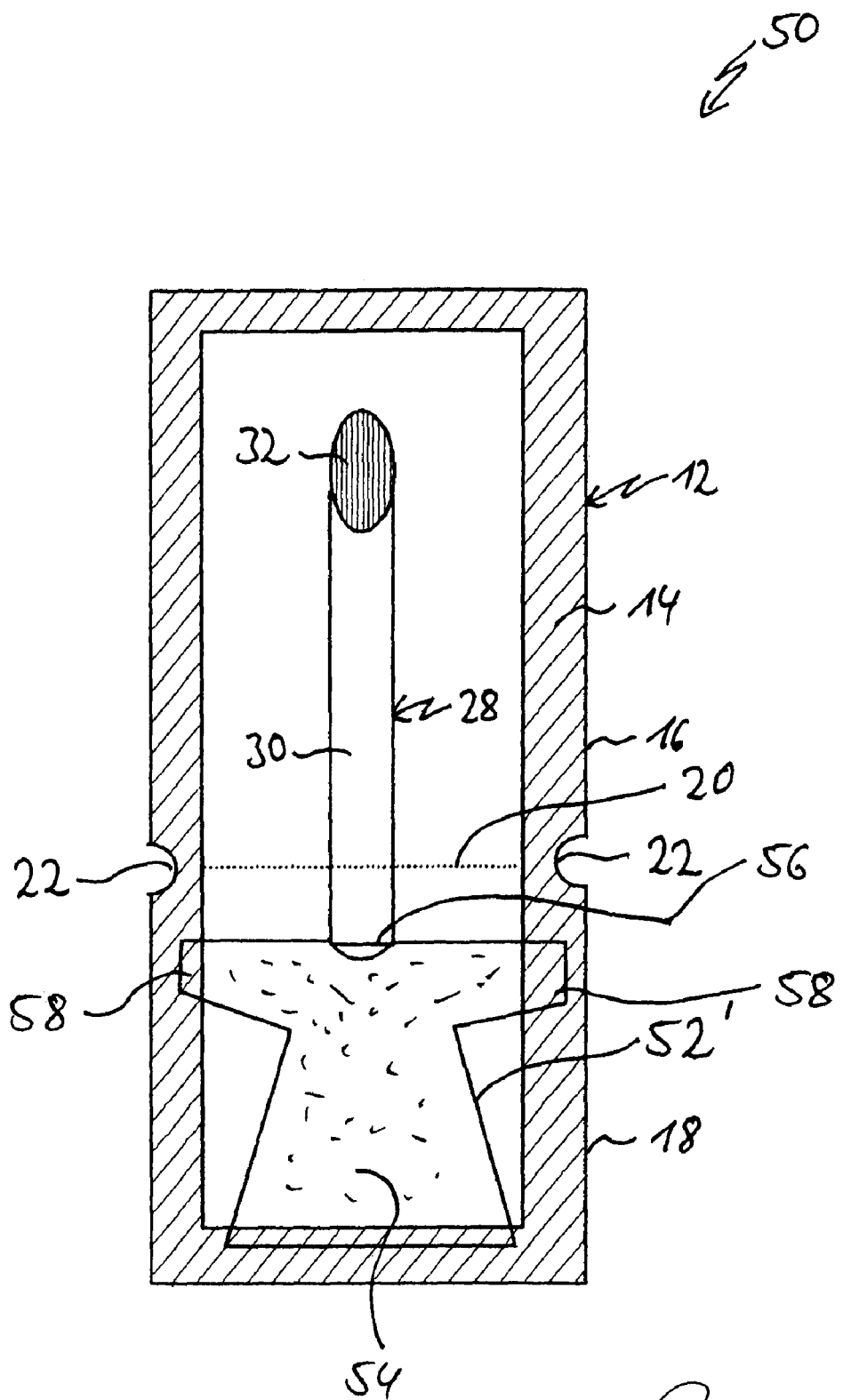
FIG. 3 is a diagrammatic illustration of another embodiment of a likewise pack-type device in accordance with the invention.

Referring now to FIG. 3 there is illustrated a further embodiment of a device 50 configured in accordance with the invention substantially the same as that as shown in FIG. 2, but differing therefrom in that the applicator 28 is now configured in one piece with the receptacle 52' representing a separation element. For activating the applicator a designed frangible location 56 is configured in the region of the orifice of the receptacle. After tearing open the pack 12 the applicator 28 is separated from the receptacle 52' at the designed frangible location 56 to thus expose its orifice so that the application section 32 of the applicator 28 can be dipped into the receptacle 52' to wet the applicator 28 with the flowable substance.

Figure 4:
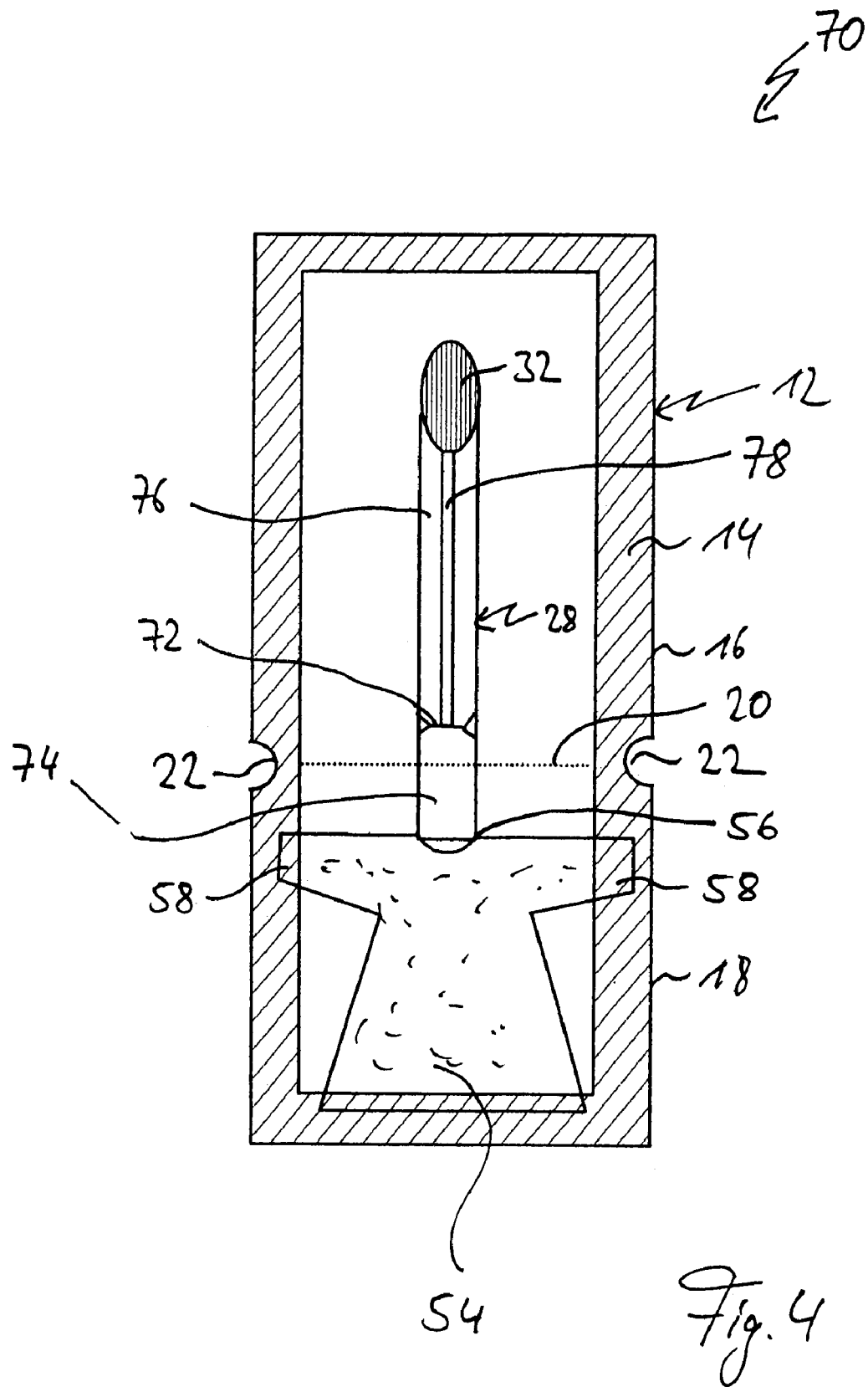
FIG. 4 is a diagrammatic illustration of yet another embodiment of a likewise pack-type device in accordance with the invention.

Referring now to FIG. 4 there is illustrated a further embodiment of a device 70 configured in accordance with the invention substantially the same as that as shown in FIG. 3, but differing therefrom in that in the region of the finger grip section 30 of the applicator 28 a second designed frangible location 72 is now provided at which a solid finger grip portion 74 can be separated from a finger grip portion 76. The finger grip portion 76 has an axial passageway 78 leading to the application portion 32 or brush hair.

To use the device 70 the pack 12 is first torn open along the tear line 20, the applicator then being parted from the receptacle 52' in the region of the designed frangible location 56. After this, the finger grip portion 74 is parted and the applicator 28 inserted by the finger grip portion 76 into the receptacle 52' via the orifice thereof. Then by manually squeezing the receptacle 52' made of flexible plastics material the flowable substance can be delivered from the receptacle 52' via the axial passageway 78 of the finger grip portion 76 to the application section 32 and applied.

Figure 5:
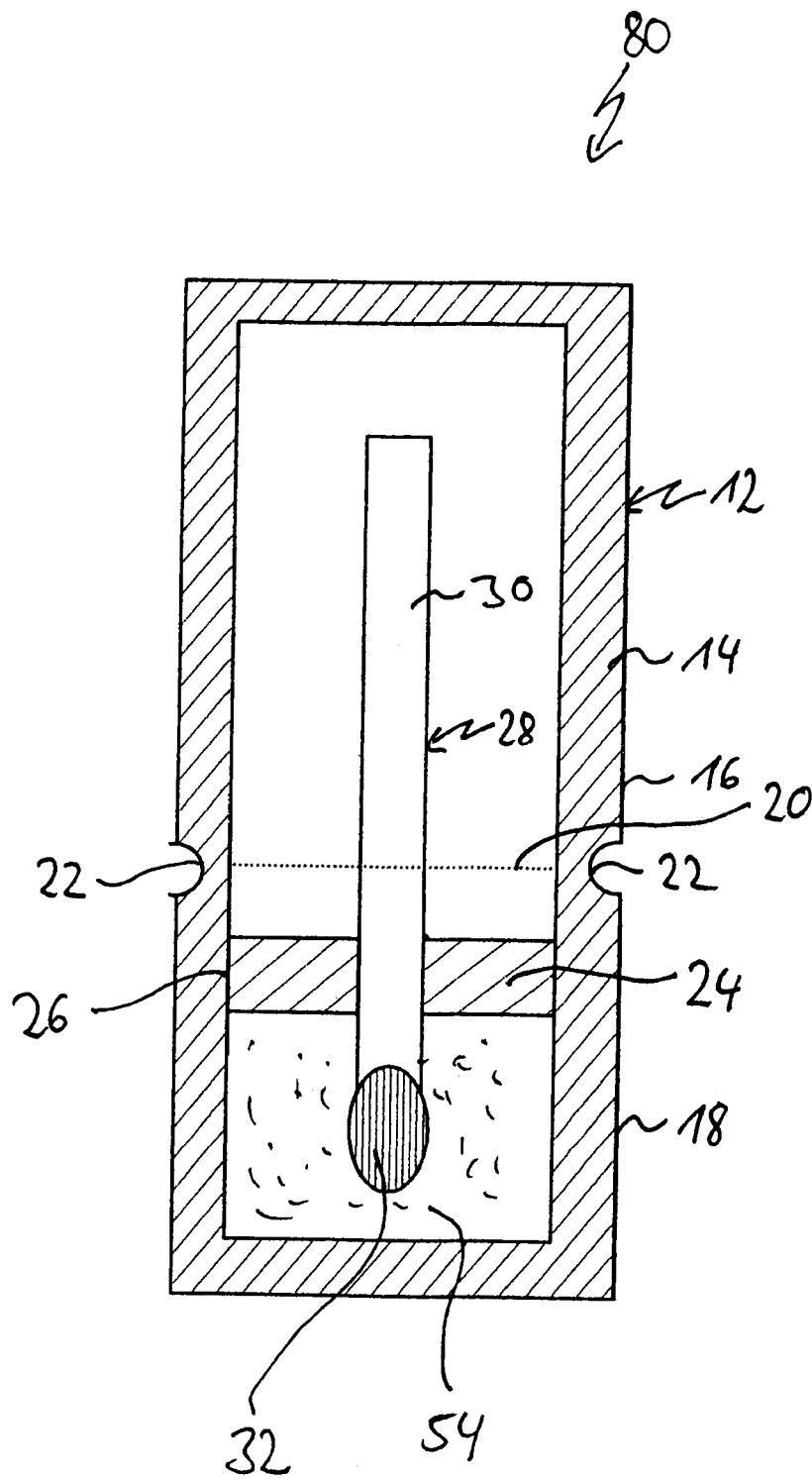
FIG. 5 is a diagrammatic illustration of still another embodiment of a likewise pack-type device in accordance with the invention.

Referring now to FIG. 5 there is illustrated a further embodiment of a device 80 serving to receive and apply a flowable substance. Disposed between the dry portion and wet portion in this device 50 is a disc-type insert 24 representing a separation element which is connected to the foil blanks of the pack 12 by a sealing seam 26 oriented crosswise.

A brush-type applicator 28 passes through the lenticular insert 24, the applicator 28 comprising a finger grip section 30 arranged in the dry portion or closure section and an application section 32 made of brush hair which is dipped into the substance to be applied within the wet portion 18 arranged in the receiving section. The insert 24 may comprise (not shown) webs on both sides welded into the side edge portions or sealing seams of the pack.

In the closed condition of the device 10 a portion of the finger grip section 30 of the brush 28 is in a positive press fit in a recess 42 of the insert 24 so that no liquid can escape from the wet section 18 into the dry section 16. The diameter of the recess 42 corresponds to the diameter of the finger grip section 30 of the applicator 28 so that the applicator 28 is held sealed tight in the press fit in the insert 24.

While there has been shown and described what are at present considered the preferred embodiments of the invention, it will be obvious to those skilled in the art that various changes and modifications can be made therein without departing from the scope of the invention defined by the appended claims.

I claim:

1. A device for applying liquid, pasty or other flowable substance including a first pack with a receiving section sealed by a sealing seam, said first pack comprising a wet portion for receiving the substance and a closure section defining a dry portion, the closure section being separated from the receiving section by a tear line, the wet portion being separated from the dry portion by a separation element, comprising an orifice closed off by a closure element which is releasable from the separation element after tearing open the first pack along the tear line, wherein the separation element is a receptacle defining a receiving space, forming a primary pack welded in the sealing seam of the first pack for the flowable substance and the first pack forms a secondary pack for the flowable substance.

2. The device as set forth in claim 1, in which the closure element is an applicator fully incorporated in the first pack and featuring an application section and a finger grip section located in the dry portion of the first pack, the orifice of the separation element being designed to engage or connect the application section of the applicator in and with the wet portion respectively.

3. The device as set forth in claim 2, in which the application section of the applicator dips into the wet portion and the finger grip section of the applicator sealingly passing through the orifice of the separation element.

4. The device as set forth in claim 2, in which the application section of the applicator is located in the dry portion and the finger grip section of the applicator closes off the orifice of the separation element by its end facing away from the application section.

5. The device as set forth in claim 4, in which the finger grip section forms a plug for the orifice of the separation element.

6. The device as set forth in claim 4, in which the finger grip section is produced in one piece with the separation element from which it is separated by at least one designed frangible location so that parting the applicator from the separation element releases the orifice.

7. The device as set forth in claim 2, in which the applicator is configured as a brush and the application section is formed by at least one of a brush hair, a flock coating, and a foam.

8. The device as set forth in claim 7, in which the brush hair is molded to the finger grip section.

9. The device as set forth in claim 2, in which the finger grip section comprises an axial passageway.

10. The device as set forth in claim 1, in which the separation element is sealed to the first pack.

11. The device as set forth in claim 1, in which the separation element is a tubular part closed off at one end, defining the receiving space and which is connected to the first pack proximal its closed end.

12. The device as set forth in claim 1, in which the pack is formed by two foil blanks edge-sealed on all sides.

13. The device as set forth in claim 12, in which the foil blanks are each made of a foil laminate.

14. The device as set forth in claim 13, in which the foil laminate is an aluminum laminate.

15. The device as set forth in claim 12, in which the foil blanks include level a sealing seam oriented crosswise to a centerline of an applicator and level with the separation element.

16. The device as set forth in claim 12, in which the tear line is defined by at least one tear nick proximal a sealing seam of the foil blanks.

* * * * *